United States Patent
Eggers

(10) Patent No.: US 8,539,672 B2
(45) Date of Patent: Sep. 24, 2013

(54) METHOD FOR IMPROVING ACCURACY IN A PERISTALTIC PUMP SYSTEM BASED ON TUBING MATERIAL PROPERTIES

(75) Inventor: Philip Eggers, Cottonwood Heights, UT (US)

(73) Assignee: Zevex, Inc., Salt Lake City, UT (US)

( * ) Notice: Subject to any disclaimer, the term of this patent is extended or adjusted under 35 U.S.C. 154(b) by 99 days.

(21) Appl. No.: 13/248,726

(22) Filed: Sep. 29, 2011

(65) Prior Publication Data

US 2012/0079719 A1    Apr. 5, 2012

Related U.S. Application Data

(60) Provisional application No. 61/388,888, filed on Oct. 1, 2010.

(51) Int. Cl.
*B23P 15/00* (2006.01)

(52) U.S. Cl.
USPC ............. 29/888.02; 29/888; 29/890.144; 29/890.147; 435/293.1

(58) Field of Classification Search
USPC .............. 29/888, 888.02, 890.144, 890.147; 435/293.1, 295.3, 383
See application file for complete search history.

(56) References Cited

U.S. PATENT DOCUMENTS

| | | |
|---|---|---|
| 2,899,907 A | 8/1959 | Becher |
| 3,050,066 A | 8/1962 | Koehn |
| 3,736,930 A | 6/1973 | Georgi |
| 3,768,934 A | 10/1973 | Magerle |
| 3,790,313 A | 2/1974 | Magerle |
| 3,915,171 A | 10/1975 | Shermeta |
| RE29,207 E | 5/1977 | Bolduc et al. |
| 4,187,057 A | 2/1980 | Xanthopoulos |
| 4,217,993 A | 8/1980 | Jess et al. |
| 4,229,299 A | 10/1980 | Savitz et al. |
| 4,315,513 A | 2/1982 | Nawash et al. |
| 4,356,824 A | 11/1982 | Vazquez |
| D272,850 S | 2/1984 | Kulle |
| 4,447,191 A | 5/1984 | Bilstad et al. |
| 4,469,481 A | 9/1984 | Kobayashi |
| 4,498,843 A | 2/1985 | Schneider et al. |
| 4,509,514 A | 4/1985 | Brain |
| 4,529,401 A | 7/1985 | Leslie et al. |
| 4,555,242 A | 11/1985 | Saudagar |

(Continued)

FOREIGN PATENT DOCUMENTS

| | | |
|---|---|---|
| CA | 1098003 | 9/1977 |
| DE | 2447005 | 10/1974 |

(Continued)

OTHER PUBLICATIONS

WIPO, International Searching Authority ISA/KR, International Search Report issued Apr. 26, 2012 in International Application No. PCT/US2011/054037.

(Continued)

*Primary Examiner* — Richard Chang
(74) *Attorney, Agent, or Firm* — Hodgson Russ LLP

(57) ABSTRACT

A method for forming peristaltic pump cassettes includes cutting tubing segments to different lengths based on the physical properties of the individual tubing segments. The size variations compensate for the physical parameters of the tube and improve accuracy in a peristaltic pump using the cassettes.

20 Claims, 7 Drawing Sheets

(56) References Cited

U.S. PATENT DOCUMENTS

| | | |
|---|---|---|
| 4,575,371 A | 3/1986 | Nordqvist et al. |
| D284,221 S | 6/1986 | Kerkut |
| 4,601,700 A | 7/1986 | Thompson et al. |
| 4,654,027 A | 3/1987 | Dragan et al. |
| 4,798,592 A | 1/1989 | Parks |
| 4,813,935 A | 3/1989 | Haber et al. |
| 4,826,500 A | 5/1989 | Rautsola |
| 4,848,343 A | 7/1989 | Wallsten et al. |
| 4,850,807 A | 7/1989 | Frantz |
| 4,850,953 A | 7/1989 | Haber et al. |
| 4,857,818 A | 8/1989 | Hobbs |
| 4,861,334 A | 8/1989 | Nawaz |
| 4,870,953 A | 10/1989 | DonMicheal et al. |
| 4,884,013 A | 11/1989 | Jackson et al. |
| 4,910,682 A | 3/1990 | Wolff et al. |
| 4,913,703 A | 4/1990 | Pasqualucci |
| 4,919,650 A | 4/1990 | Feingold et al. |
| 4,927,412 A | 5/1990 | Menasche |
| 4,976,687 A | 12/1990 | Martin |
| 4,976,710 A | 12/1990 | Mackin |
| 5,000,349 A | 3/1991 | Rautsola |
| D319,312 S | 8/1991 | Schneider |
| 5,074,845 A | 12/1991 | Miraki et al. |
| 5,080,650 A | 1/1992 | Hirsch et al. |
| 5,099,184 A | 3/1992 | Hornung et al. |
| 5,125,897 A | 6/1992 | Quinn et al. |
| 5,137,522 A | 8/1992 | Bron |
| 5,154,725 A | 10/1992 | Leopold |
| 5,171,222 A | 12/1992 | Euteneuer et al. |
| 5,195,960 A | 3/1993 | Hossain et al. |
| 5,201,711 A | 4/1993 | Pasqualucci |
| 5,226,889 A | 7/1993 | Sheiban |
| 5,244,463 A | 9/1993 | Cordner, Jr. et al. |
| 5,254,992 A | 10/1993 | Keen et al. |
| 5,261,879 A | 11/1993 | Brill |
| 5,267,983 A | 12/1993 | Oilschlager et al. |
| 5,279,556 A | 1/1994 | Goi et al. |
| 5,308,325 A | 5/1994 | Quinn et al. |
| 5,312,334 A | 5/1994 | Hara et al. |
| 5,314,405 A | 5/1994 | Kriesel et al. |
| 5,320,503 A | 6/1994 | Davis |
| 5,324,258 A | 6/1994 | Rohrbough |
| 5,336,181 A | 8/1994 | Nakao et al. |
| 5,336,203 A | 8/1994 | Goldhardt et al. |
| 5,342,321 A | 8/1994 | Potter |
| 5,344,420 A | 9/1994 | Hilal et al. |
| 5,350,362 A | 9/1994 | Stouder, Jr. |
| 5,355,735 A | 10/1994 | Miller et al. |
| 5,356,391 A | 10/1994 | Stewart |
| 5,358,488 A | 10/1994 | Suriyapa |
| 5,370,612 A | 12/1994 | Maeda et al. |
| 5,391,159 A | 2/1995 | Hirsch et al. |
| 5,395,320 A | 3/1995 | Padda et al. |
| D357,312 S | 4/1995 | Riquier et al. |
| 5,403,290 A | 4/1995 | Noble |
| 5,411,491 A | 5/1995 | Goldhardt et al. |
| 5,413,565 A | 5/1995 | Michels et al. |
| 5,438,868 A | 8/1995 | Holden et al. |
| 5,449,370 A | 9/1995 | Vaitekunas |
| 5,458,583 A | 10/1995 | McNeely et al. |
| 5,472,403 A | 12/1995 | Cornacchia et al. |
| 5,472,447 A | 12/1995 | Abrams et al. |
| 5,482,446 A | 1/1996 | Williamson et al. |
| 5,505,707 A | 4/1996 | Manzie et al. |
| 5,514,102 A | 5/1996 | Winterer et al. |
| 5,531,680 A | 7/1996 | Dumas et al. |
| 5,538,405 A | 7/1996 | Patno et al. |
| 5,549,657 A | 8/1996 | Stern et al. |
| 5,556,385 A | 9/1996 | Andersen |
| D374,718 S | 10/1996 | Dodge et al. |
| 5,575,631 A | 11/1996 | Jester |
| 5,630,710 A | 5/1997 | Tune et al. |
| 5,657,000 A | 8/1997 | Ellingboe |
| 5,683,233 A | 11/1997 | Moubayed et al. |
| D388,876 S | 1/1998 | Sampson |
| D389,228 S | 1/1998 | Winterer et al. |
| 5,704,584 A | 1/1998 | Winterer et al. |
| 5,714,110 A | 2/1998 | Wang et al. |
| 5,718,691 A | 2/1998 | Russo |
| 5,720,721 A | 2/1998 | Dumas et al. |
| 5,728,130 A | 3/1998 | Ishikawa et al. |
| 5,733,061 A | 3/1998 | Child |
| 5,746,756 A | 5/1998 | Bromfield et al. |
| 5,769,816 A | 6/1998 | Barbut et al. |
| 5,789,675 A | 8/1998 | Blaine et al. |
| 5,791,881 A | 8/1998 | Moubayed et al. |
| 5,800,408 A | 9/1998 | Strauss et al. |
| 5,810,323 A | 9/1998 | Winterer et al. |
| 5,836,924 A | 11/1998 | Kelliher et al. |
| 5,853,386 A | 12/1998 | Davis et al. |
| 5,865,816 A | 2/1999 | Quinn |
| 5,924,852 A | 7/1999 | Moubayed et al. |
| 5,935,106 A | 8/1999 | Olsen |
| 5,996,650 A | 12/1999 | Phallen et al. |
| 5,997,503 A | 12/1999 | Willis et al. |
| 5,997,546 A | 12/1999 | Foster et al. |
| 6,007,521 A | 12/1999 | Bidwell et al. |
| 6,017,326 A | 1/2000 | Pasqualucci |
| 6,019,746 A | 2/2000 | Picha et al. |
| 6,023,970 A | 2/2000 | Blaine |
| 6,030,359 A | 2/2000 | Nowosielski |
| 6,056,724 A | 5/2000 | Lacroix |
| 6,121,739 A | 9/2000 | Haberlander |
| 6,126,631 A | 10/2000 | Loggie |
| 6,142,979 A | 11/2000 | McNally et al. |
| 6,149,627 A | 11/2000 | Uber |
| 6,164,921 A | 12/2000 | Moubayed et al. |
| 6,192,752 B1 | 2/2001 | Blaine |
| 6,261,262 B1 | 7/2001 | Briggs et al. |
| 6,328,720 B1 | 12/2001 | McNally et al. |
| D455,489 S | 4/2002 | Beck et al. |
| 6,371,732 B1 | 4/2002 | Moubayed et al. |
| 6,416,293 B1 | 7/2002 | Bouchard et al. |
| 6,506,035 B1 | 1/2003 | Beck |
| 6,523,414 B1 | 2/2003 | Malmstrom et al. |
| 6,531,708 B1 | 3/2003 | Malmstrom et al. |
| 6,595,950 B1 | 7/2003 | Miles et al. |
| 6,623,447 B2 | 9/2003 | Miles et al. |
| 6,636,010 B1 | 10/2003 | Malmstrom et al. |
| 6,659,976 B2 | 12/2003 | Beck et al. |
| 6,682,500 B2 | 1/2004 | Soltanpour et al. |
| D487,149 S | 2/2004 | Farris |
| 6,685,670 B2 | 2/2004 | Miles et al. |
| 6,749,591 B1 | 6/2004 | McNally et al. |
| 6,750,468 B2 | 6/2004 | Malmstrom et al. |
| 6,808,521 B1 | 10/2004 | McMichael |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,942,636 B2 | 9/2005 | Holst et al. |
| 6,979,311 B2 | 12/2005 | Miles et al. |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| D536,783 S | 2/2007 | Cise et al. |
| 7,207,780 B2 | 4/2007 | Bach |
| 7,367,963 B2 | 5/2008 | Cise et al. |
| 7,530,968 B2 | 5/2009 | Gonnelli |
| 7,556,619 B2 | 7/2009 | Spohn et al. |
| 7,718,430 B2 * | 5/2010 | Antwiler ............ 435/383 |
| 2002/0010420 A1 | 1/2002 | Bagaoisan et al. |
| 2002/0107501 A1 | 8/2002 | Smith et al. |
| 2002/0169424 A1 | 11/2002 | Miles et al. |
| 2003/0212381 A1 | 11/2003 | Whitehead |
| 2004/0019318 A1 | 1/2004 | Wilson et al. |
| 2004/0054350 A1 | 3/2004 | Shaughnessy et al. |

| | | |
|---|---|---|
| 2004/0220542 A1 | 11/2004 | Cise et al. |
| 2005/0004540 A1 | 1/2005 | McNally |
| 2005/0096593 A1 | 5/2005 | Pope et al. |
| 2005/0119625 A1 | 6/2005 | Miles et al. |
| 2005/0209563 A1 | 9/2005 | Hopping et al. |
| 2005/0277912 A1 | 12/2005 | John |
| 2006/0058740 A1 | 3/2006 | Cise |
| 2006/0142692 A1 | 6/2006 | Jacobson et al. |
| 2006/0200073 A1 | 9/2006 | Radmer et al. |
| 2007/0118078 A1 | 5/2007 | McNally |
| 2007/0151346 A1 | 7/2007 | Malmstrom et al. |
| 2008/0051711 A1 | 2/2008 | Mounce et al. |
| 2008/0058720 A1 | 3/2008 | Spohn et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2009/0049919 A1 | 2/2009 | Hills |
| 2009/0149801 A1 | 6/2009 | Crandall |
| 2009/0254034 A1 | 10/2009 | Beck |
| 2010/0005655 A1 | 1/2010 | Nguyen |

FOREIGN PATENT DOCUMENTS

| | | |
|---|---|---|
| DE | 20000965 U1 | 1/2000 |
| GB | 2 338 759 | 12/1999 |
| JP | 05-042219 | 2/1993 |
| JP | 10-048759 | 2/1998 |
| WO | WO 96/08666 | 3/1996 |

OTHER PUBLICATIONS

The International Bureau of WIPO, International Preliminary Report on Patentability issued in International Application No. PCT/US2011/054037 Apr. 2, 2013.

* cited by examiner

METHOD FOR IMPROVING ACCURACY IN A PERISTALTIC PUMP SYSTEM BASED ON TUBING MATERIAL PROPERTIES

RELATED APPLICATIONS

The present application claims the benefit of U.S. Provisional Patent Application No. 61/388,888, filed Oct. 1, 2010, which is herein incorporated by reference in its entirety.

BACKGROUND OF THE INVENTION

1. The Field of the Invention

The present invention relates to a method for improving accuracy in a peristaltic pump. More specifically, the present invention relates to a method for reducing variance in the output of a pump due to physical parameters of the tubing.

2. State of the Art

Peristaltic pumps are used in a wide variety of applications due to their ability to deliver a relatively high degree of accuracy in dosing. Peristaltic pumps usually utilize resilient tubing with walls which define a fluid flow lumen having a diameter falling within a specified range of tolerances. The tubing is often made from silicone or similar polymers which allow compression and a relatively quick return to the tubing's original shape. During fluid delivery, the tubing is held in engagement with a pumping member which selectively compresses a portion of the tubing to expel the fluid from that portion of the fluid flow lumen and to drive the fluid through the lumen downstream. Once the pumping member disengages a portion of the tubing, the tubing resumes its original shape and the lumen is filled with additional fluid.

In a linear or curvi-linear peristaltic pump, as shown generally at 10 in FIG. 1A, the piece of tubing 14 may be wrapped or stretched over a plurality of engagement members or pumping fingers 18. The engagement members 18 sequentially extend into the tubing 14 to collapse the tubing and move the fluid downstream. As the engagement members 18 retract, the resilient tubing 14 returns to its normal cross-section, thereby allowing the lumen to fill with fluid which will be moved during the next cycle. The segment of the tubing 14 which is collapsed by the engagement members 18 provides a relatively known volume of fluid in the lumen. Thus, each cycle of the engagement member moves a certain amount of fluid and repeating the cycle multiple times will deliver a desired dose. A more detailed discussion of operation of a curvilinear pump is found in U.S. Pat. No. 6,164,921.

In rotary peristaltic pumps, as shown in FIG. 1B, the tubing 14 is often anchored at opposing ends 14a and 14b to a pump body 20. The anchoring may be accomplished by connectors 24 which connect the resilient tubing 14 to other tubing. (Silicone tubing is often more expensive than other types of tubing so it is economical to use the silicone tubing only for the portion which is disposed on the pump). Between opposing ends 14a and 14b, the tubing is wrapped around a rotor 28 which has a plurality of engagement members or rollers 38, 38a, 38b. As the rollers move around the rotors, the rollers will pinch the tubing and collapse the lumen (as represented by roller 38a). This results in a relatively known quantity of fluid being disposed in the lumen of the tubing section 14c disposed between roller 38a and 38b. As the roller 38a continues to move into the position shown by roller 38, the roller continues collapsing the tubing and forcing fluid in the lumen forward. Thus each third rotation of the rotor 28 delivers a substantially known quantity of fluid downstream. Thus, a user can obtain a desired dose by simply controlling the number of rotations of the rotor. A more detailed explanation of the functioning of a rotary peristaltic pump can be found in U.S. Pat. No. 5,720,721.

While peristaltic pumps are relatively accurate, their accuracy depends in large part on the physical properties of the tubing and physical conditions along the tubing. For example, U.S. Pat. No. 5,720,721 teaches a plurality of pressure sensors 42 which are disposed upstream and downstream from the rotor to detect pressure changes within the tubing which can affect the amount of fluid which is moved with each rotation of the tubing. Bubble detectors 46 can also be used to ensure that the proper amount of liquid is being moved and/or that undesirable air, etc., is not present.

In addition to pressure within the tubing and material within the fluid being pumped, the physical parameters of the tubing itself can have an effect on accuracy. These physical parameters can include the thickness of the wall which defines the lumen, the diameter of the lumen (i.e. interior diameter of the tubing), the length of the tubing, and material properties of the tubing such as the durometer rating (generally related to the compressibility of the tubing) and Young's modulus (generally related to the stretchability of the tubing).

Each of the physical parameters or properties can affect the accuracy of fluid delivery by the pump. For example, if a tube has a larger inner diameter than another tube, it will carry a larger volume of fluid with each cycle of the peristaltic pump due to the larger cross-sectional area. Likewise, variances in the collapsibility of the tubing will affect the amount of solution which is passed through the tubing with each cycle of the pump. Additionally, length is important because stretching the tube will naturally reduce the inner diameter of the tube and reduce the amount of fluid moved with each pump cycle. However, a more stretchable tube can actually deliver a slightly higher amount of fluid with each cycle.

Because the physical parameters of the tubing can have a marked impact on the actual flow volume through the pump, it is common for those making peristaltic pump cassettes or feeding lines for use in medical pumps and other pumps that require a high degree of accuracy to require that tubing stock fall within certain parameters. For example, a company manufacturing an enteral feeding pump cassette or infusion pump cassette, may purchase tubing and require that it be delivered in lengths of 5 inches, ±0.040 inches, having an outer diameter of 0.200 inches, ±0.003 inches, an inner diameter of 0.120 inches, ±0.003 inches, and have a durometer rating of Shore A 50, ±5.

While the variances allowed in the tubing specifications are relatively small, each may have an impact of the volumetric accuracy of the pump. For example, the difference in tubing wall thickness may result in a 2% change in output. Likewise differences in the durometer rating or Young's modulus of the tubing may create a 2% variation in output. When each of the variables is added together, the variations in the tubing can result in a variance of between 5-10% of the total flow output of the tubing.

While it will be appreciated that accuracy of the pump can be increased by further reducing the tolerances in which the tubing must fall, requiring manufacturers to provide tubing more closely meeting the tolerances typically results in a much higher purchase price for the tubing thereby increasing the cost of peristaltic pumping sets for the end user.

Thus, there is a need for a method for improving the accuracy of a peristaltic pump when using tubing falling within a predetermined set of parameters.

SUMMARY OF THE INVENTION

In accordance with the principals of the current invention, it has been found that increased accuracy in fluid delivery in a peristaltic pump can be achieved by cutting the tubing at least in part based on physical characteristics rather than at a set predetermined length under ambient conditions.

In accordance with one aspect of the invention, the tubing is stretched subject to a predetermined or known force. The stretched tubing is then cut to a predetermined length and released. Once released the tubing returns to a non-stretched state. Tubing having various differences in diameter and elasticity will have somewhat varying lengths. However, the tubing incorporated into a feeding cassette provides more consistent dosing as variations in the physical properties of the tubing are at least partially offset by the differences in length.

In accordance with one aspect of the invention, the tubing is provided in bulk. The tubing is braced with a predetermined length of tubing extending beyond the brace. The tubing is then stretched by a predetermined or known force and cut (e.g. cut at 6 inches stretched) so that the cut portion of the tubing is a desired length (e.g. 5 inches, ±0.1 inches) when the tubing is allowed to return to its length under ambient conditions. Because it will stretch more, a tube having greater ability to stretch may be 4.9 inches in its ambient state, while tubing which is less stretchable may be 5.1 inches in ambient conditions. The tubing segments are then attached to a pump cassette for use, the difference in the length offsetting the variance in the other physical parameters of the tubing. It will be understood as used herein that a pump cassette may refer to a portion of a feeding or infusion set which includes a pump tubing segment which is formed as a peristalsis loop, a linear pump tubing segment which is mounted along a pumping mechanism, or other pump tubing segments which engage a peristaltic pump.

In accordance with one aspect of the invention, the tubing is first mounted at one end on a pump cassette. The tubing is then stretched under a known force and cut at a predetermined or known length. The cut end of the tubing is attached to another connector on the pump cassette either prior to or after the tubing has retracted to its ambient length.

In accordance with another aspect of the invention the tubing is mounted or braced at one end and stretched under a predetermined force which is determined by a known physical characteristic of the tubing, such as, for example, Young's modulus or durometer rating, a precise tubing dimension, etc. of the tubing.

In accordance with another aspect of the invention, the tubing is stretched to a predetermined length under variable force. The force necessary to achieve the desired stretch is noted and the tubing is cut based on force necessary to obtain the desired stretch. The cut tubing segment is then loaded on the pump cassette and used in a peristaltic pump. The different tube lengths help offset the variances in the tubing. The cut can be performed while pulling the tubing from feedstock with the tubing being braced at one end, or one end of the tubing may be attached to a portion of the pump cassette, stretched and cut, and then mounted to the opposing end of the cassette.

In accordance with yet another aspect of the invention, the tubing is stretched to a predetermined length under a variable force. The force necessary to achieve the desired stretch is noted and combined with information based on at least one known physical parameter of the tubing, e.g. Young's modulus or durometer rating, a precise tubing dimension, etc. and then a cut position is determined and the tubing is cut.

These and other aspects of the present invention may be realized in a method for improving accuracy in a peristaltic pump as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single FIGURE, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1A:
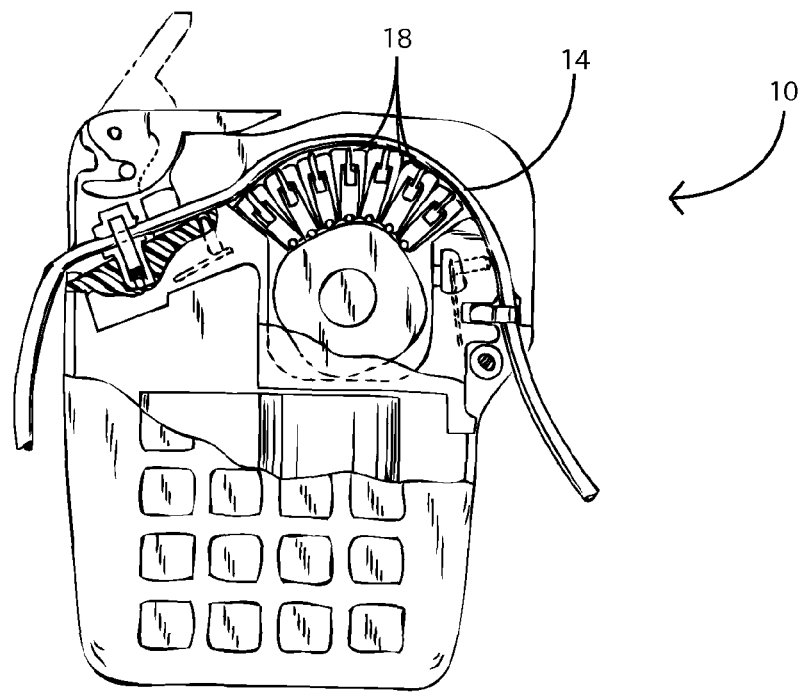
FIG. 1A shows a side, partially cut-away view of a curvilinear peristaltic pump formed in accordance with the teachings of the prior art.
Figure 1B:
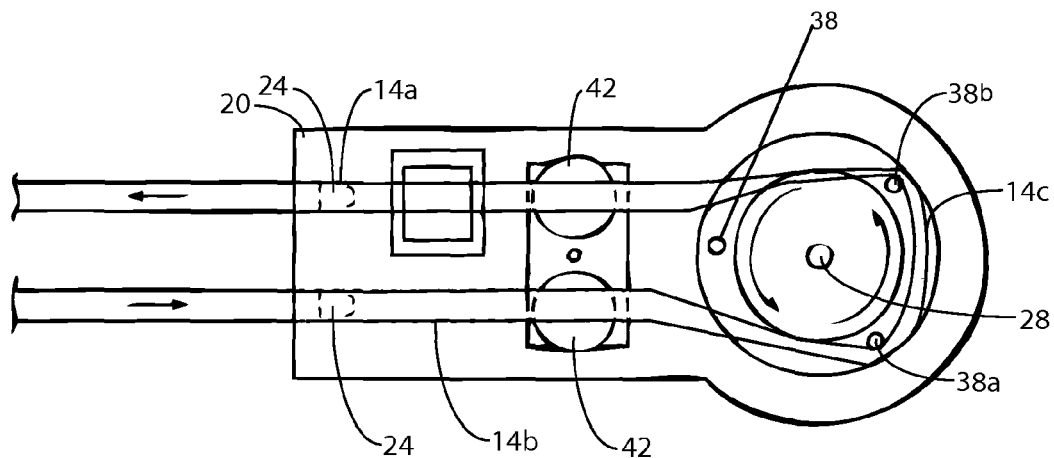
FIG. 1B shows a top view of a rotary peristaltic pump and pump cassette formed in accordance with the teachings of the prior art.
Figure 2:
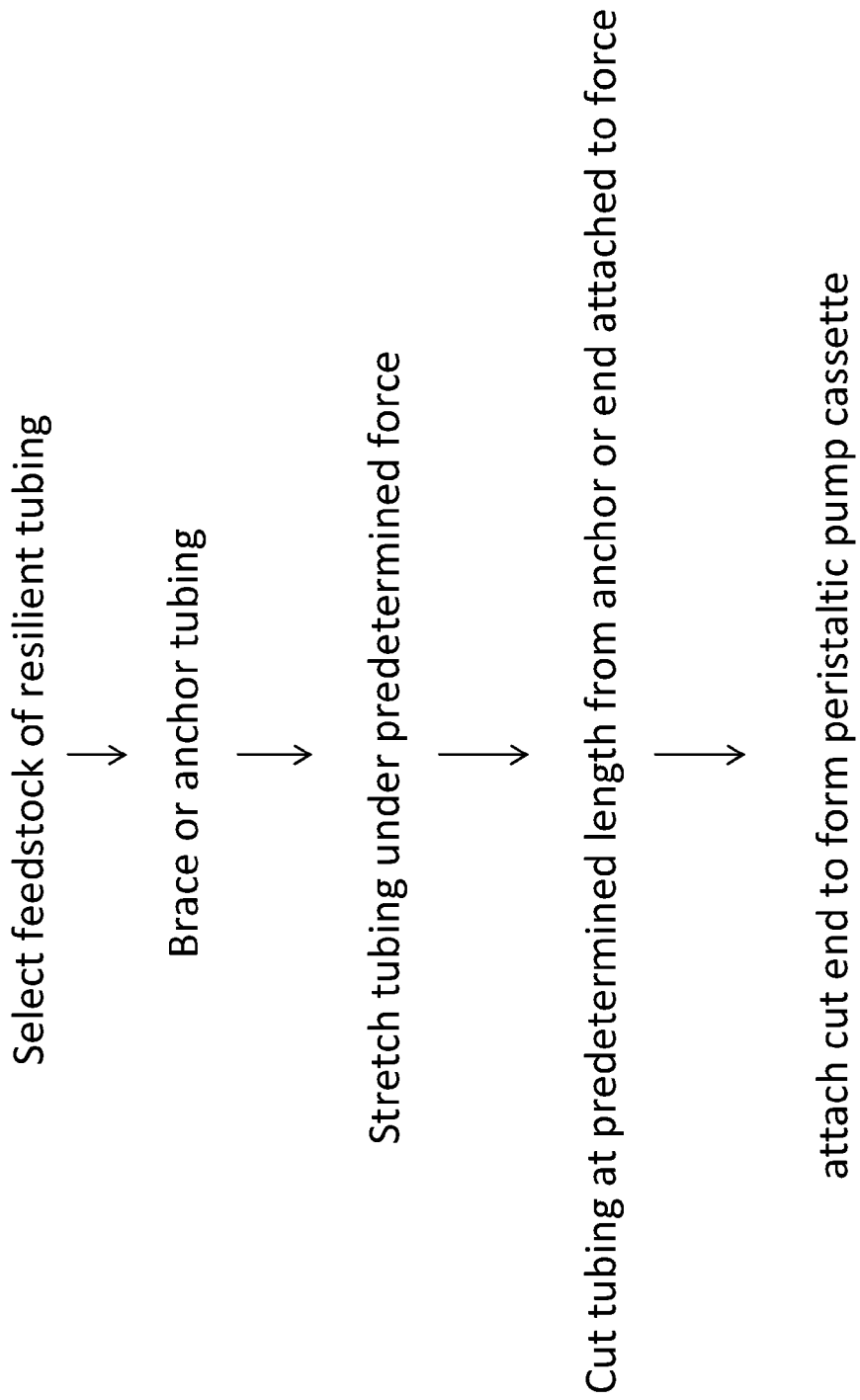
FIG. 2 shows a flowchart of a method of forming a tubing segment for use in a peristaltic pump

Turning now to FIG. 2, there is shown a flowchart of a method of forming a tubing segment for use in a peristaltic pump. The first step of the method is to select a feedstock of tubing which falls within general tolerances. For example, a manufacturer of enteral feeding pump cassettes may have ordered tubing having an outer diameter of 0.200 inches, ±0.003 inches, an inner diameter of 0.120 inches, ±0.003 inches, and have a durometer rating of Shore A 50, ±5.

The selected feedstock of resilient tubing may be on a roll or may be in precut segments. Either way, the tubing should conform generally to the tolerance specifications specified by the manufacturer. This will allow a given accuracy range to be present for the tubing prior to implementing the steps of the present invention.

Once the feedstock is selected, the tubing is braced or anchored. This may be done by attaching the tubing to a brace member or by attaching the tubing to a connector, such as a connector of a peristaltic pump cassette or adaptor.

Once the tubing is braced or anchored, the tubing may be subjected to a predetermined force to stretch the tubing. For example, applying a five pound force to a tubing segment approximately 5.5 inches long will cause the tube to stretch to about 6.5 inches. Depending on the physical characteristics of the tubing, the actual length of the stretched tubing segment may be 6.3 inches for one tubing segment and 6.7 inches for another tubing segment having different physical properties. This type of variation is common in inter-lot runs, but can even occur in intra-lot runs due to poor manufacturing quality control or certain environmental factors.

The stretched tubing is then cut at a predetermined length. If a five inch length of tubing is desired, the stretched tubing may be cut at 6 inches either from the brace or anchor or from the stretched end. (Obviously, if the cut is made from the brace end, the tubing would also be cut at the brace to provide the cut stretched tube segment). Once cut, the tubing may be allowed to return to its unstretched orientation. A tubing segment which is more stretchable than average will be slightly less than five inches (e.g. 4.9-4.999) in ambient conditions, and a tubing segment which is less stretchable than average will be slightly greater than five inches (e.g. 5.001 to 5.1 inches). Thus, the feeding or infusion cassettes made from the cut tubing segment will have slight differences in tubing length. However, because the differences in length correlate with the physical parameters of the tubing, the cassettes have a greater degree of accuracy, as the variation in tubing length helps offset the variations in other parameters of the tubing. For example, if the tolerances identified above normally result in a 6 percent variance in flow accuracy, forming the feeding cassette in accordance with the method of the current invention may have a 4.5 percent variance in flow accuracy. Thus, the accuracy variance is reduced by 25 percent without requiring any reduction in the variance in the feedstock.

As an alternative to the above, the tubing may be stretched under a known force that is at least partially selected based on a known physical characteristic of the tubing, such as, for example, Young's modulus or durometer rating, a precise tubing dimension, etc. of the tubing. For example, if the tubing had a known Shore-A rating of 80, the tubing may be stretched under force A, while tubing having a known Shore-A rating of 70 may be stretched under force B. Tables may be created that provide appropriate adjustments based on empirical testing to provide the appropriate force to be used for a known physical parameter.

Figure 3:
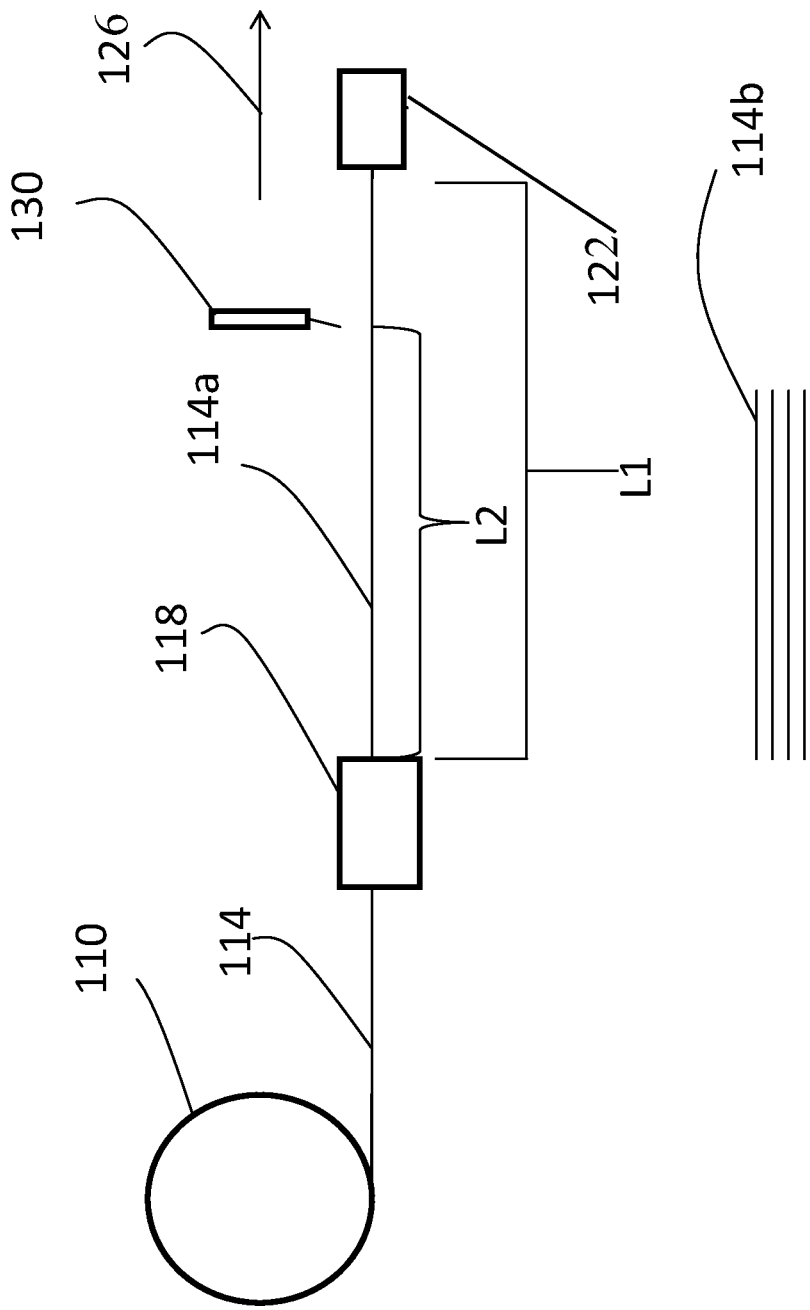
FIG. 3 shows a feedstock of bulk tubing and a tubing segment being cut in accordance with principles of the present invention.

Turning now to FIG. 3, there is shown feedstock 110 of bulk tubing 114. As was mentioned previously, the tubing may be on a roll or in precut segments. The tubing 114 is attached to a brace or anchor 118 at one end of a tubing segment 114a and to a force applicator 122 at an opposing end. The force applicator 122 can be any of a variety of mechanisms for drawing a force (as represented by arrow 126) to stretch the tubing segment 114a. These may include a drive piston, a spring, or even a simple weight. For sake of example only, the force drawn on the tubing segment 114a may be 1-10 pounds, with a force of 4-6 pounds being a presently desirable range for an enteral feeding pump cassette having the tubing specifications discussed above.

The tubing segment 114a is drawn out to a length L1 which may differ slightly for each tubing segment due to variations in the tubing's physical properties. The variations in one sample set of tubing ranged in the area of 0.04 inches per inch of tubing. Once the tubing segment 114a is stretched, a cutting instrument 130 is used to cut the tube at a predetermined location. The cut may be at the predetermined distance from the distal end to which the force applicator 122 is attached, thus resulting in a cut tube segment. In the alternative, the tubing segment may be cut at a predetermined distance from the brace or anchor 118, as represented by L2, and also cut at the brace or anchor. It will be appreciated that L1 and L2 could be the same length if the tubing segment 114a is only stretched so that the cut tubing segment is the desired length.

Once the tubing segments 114a are cut, force on the tubing segments may be removed and they will return to an ambient state as indicated at 114b. A six inch stretched tubing segment may be about, for example 4.9 to 5.1 inches and used to form a feeding pump cassette, infusion pump cassette, etc. While the tubing segment will normally be mounted in the pumping cassette in a generally ambient state (i.e. not stretched lengthwise), there are applications in which the tubing segment may be prestretched in the pump cassette.

As used herein, a cassette may include a tubing segment for a rotary peristaltic pump, which typically includes the ends of the tubing segment 114b being mounted on connectors which are disposed adjacent each other so the tubing segment forms a general U-shape (at least when mounted in the pump). However, for linear pumps, the cassette may simply be the tubing mounted to a connector at each end. The term cassette should be viewed to cover such configurations and other configurations used in peristaltic pumps.

Figure 4A:
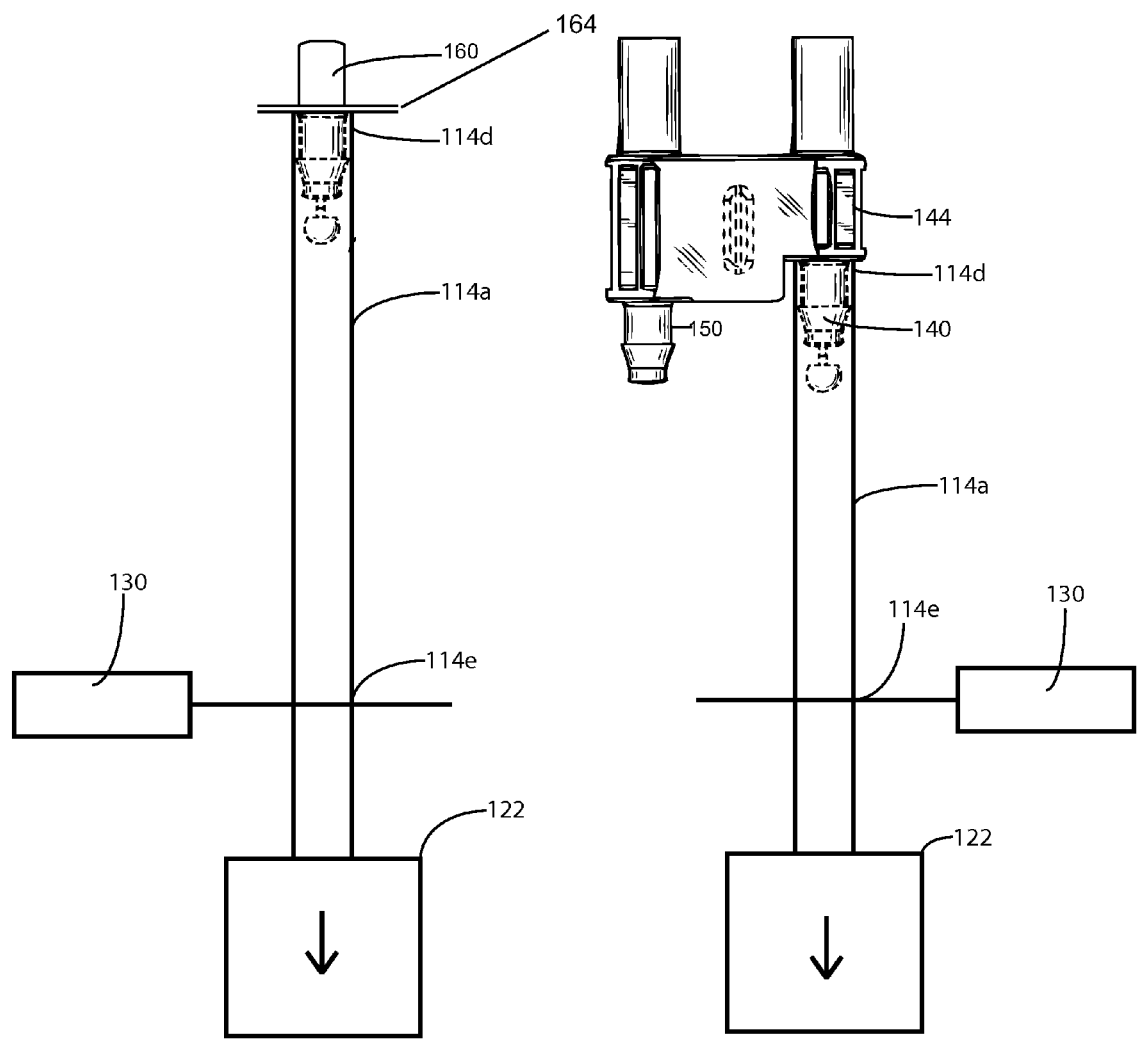
FIGS. 4A and 4B show tubing segments being cut and other portions of a peristaltic pump cassette for rotary peristaltic pumps and linear and curvilinear pumps, respectively, in accordance with principles of the present invention.
Figure 4B:
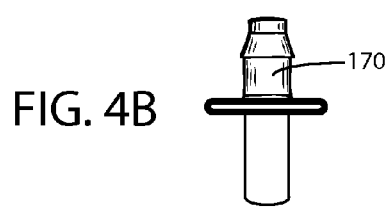

Turning now to FIGS. 4A and 4B, there are shown tubing segments 114a being cut and other portions of a peristaltic pump cassette in accordance with principles of the present invention. The tubing segment 114a may be attached at a first end 114d to a connector 140 (FIG. 4A), 160 (FIG. 4B) forming a portion of a feeding pump cassette 144, 164, respectively. A portion of the connector 140, 160 typically extends into the tubing segment 114a and is shown with dashed lines.

The cassette connector 140, 160 may be held in place and the tubing segment 114a may be subjected to a known force, such as a weight 122. The known force may be, for example, between 4 and 6 pounds. The tubing segment 114 may be cut at a predetermined distance from the connector 140 by the cutting mechanism 130. The cut end 114e may be attached to the other connector 150, thereby forming a peristaltic pump cassette tubing loop.

While the cassette 144 may be for a rotary peristaltic pump cassette, other configurations could also be made. For example, for a linear or curvilinear peristaltic pump, connectors 160, 170 are typically disposed at opposing ends of the tubing segment 114a as shown in FIG. 4B. The connectors 160, 170 may be mounted on opposing sides of the linear or curvilinear pumping mechanism to hold the tubing segment 114a securely while it is being acted on by the pumping mechanism.

Figure 5:
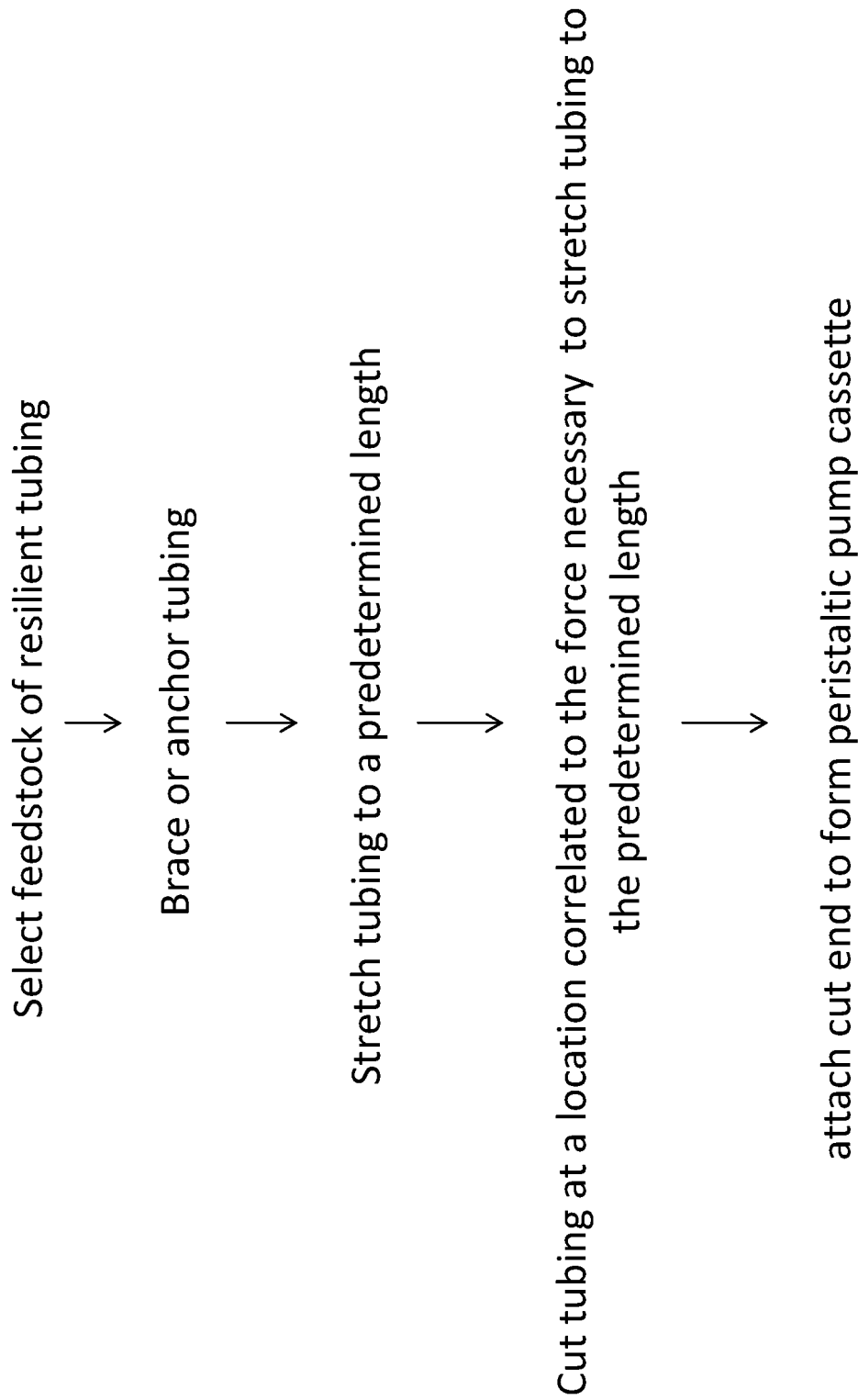
FIG. 5 shows a flowchart of a method for forming a tubing segment to improve accuracy in a peristaltic pump in accordance with the principles of the present invention.

FIG. 5 shows a flowchart of an alternate method for forming a tubing segment to improve accuracy in a peristaltic pump in accordance with the principles of the present invention. The feedstock tubing may be braced or anchored. This may be performed by attaching one end of the tubing to a connector or by bracing or anchoring a tubing segment from a bulk tubing supply. The tubing segment then may be grasped beyond a likely opposing end of a desired tubing segment and a force applied until the tubing segment reaches a predetermined length. A gauge or strain meter measures the amount of force necessary to achieve the desired length. The tubing is then cut at a position which correlates with the amount of force necessary to reach the predetermined length.

Figure 6:
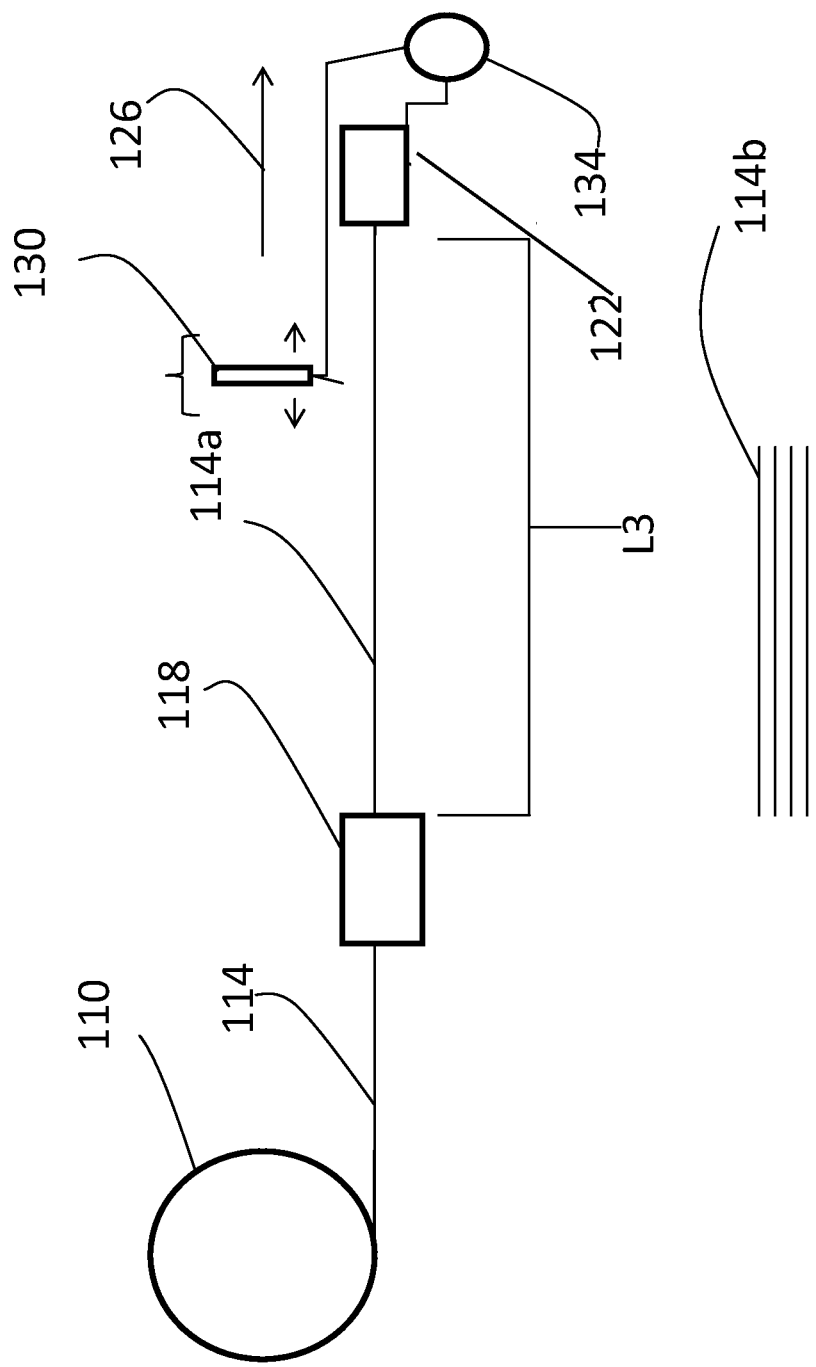
FIG. 6 shows tubing being cut at variable positions based on the pressure necessary to reach a predetermined length.

Turning to FIG. 6, there is shown tubing being cut at variable positions based on the pressure necessary to reach a predetermined length. A feedstock 110 may be used to supply tubing 114. The feedstock may be tubing on a roll, or can be straight pieces of tubing. The feedstock in any of the examples herein could even be freshly extruded tubing.

The tubing segment 114b may be captured by a brace or anchor 118. As discussed previously, this may be done on a continuous piece of tubing which is then cut, or an end of the tubing may be mounted on an anchor, such as a connector of a peristaltic pump cassette. A free end (or distal location) of the tubing segment 114a is secured by a force applicator 122 which applies force as represented by arrow 126. The tubing is stretched to a predetermined length L3 which may be, for example, 5.5 inches. The force necessary to stretch the tubing segment 114a to the desired length may be monitored by a gauge or strain meter 134. The position of the cutting mechanism 130 may be adjusted based on the force required to stretch the tubing segment 114a to the desired length and the cutting mechanism cuts the tubing segment. If the opposing end of the tubing segment 114a is not already cut, such as a piece mounted on a brace or anchor, the opposing end is cut, for example, by the brace or anchor 118. Cut tubing segments 114b may be allowed to return to their ambient length prior to attachment to connectors, etc., of a cassette.

As an alternative to the above, the tubing may be stretched to a known length at least partially selected based on a known physical characteristic of the tubing, such as, for example, Young's modulus or durometer rating, a precise tubing dimension, etc. of the tubing. For example, if the tubing had a known Shore-A rating of 80, the tubing may be stretched to length A, while tubing having a known Shore-A rating of 70 may be stretched to length B. Tables may be created that provide appropriate adjustments based on empirical testing to provide the appropriate force to be used for a known physical parameter.

Figure 7A:
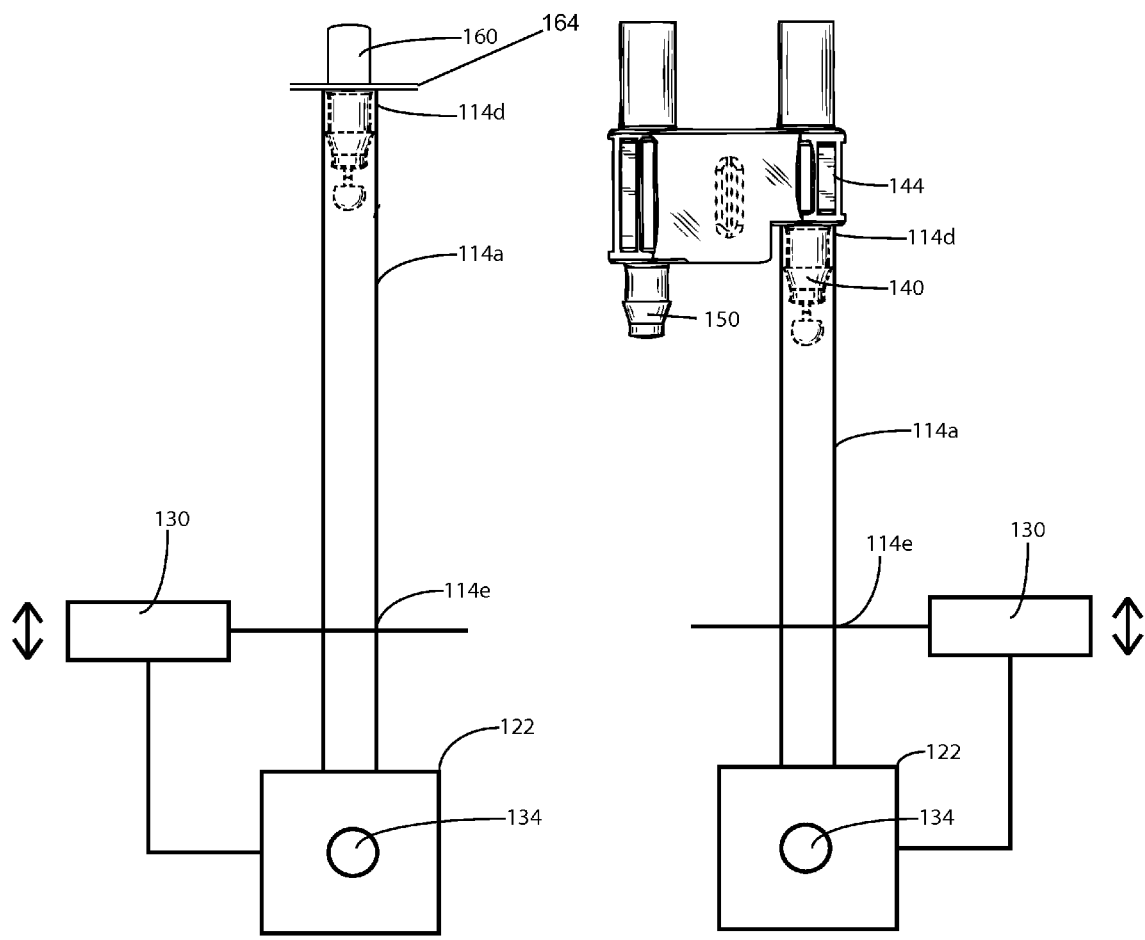
FIGS. 7A and 7B show peristaltic pump segments being formed in accordance with the method shown in FIG. 6.
Figure 7B:
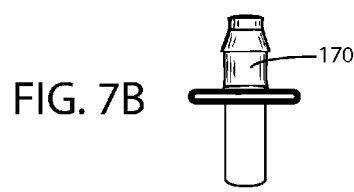

Turning now to FIGS. 7A and 7B, there are shown peristaltic feeding pump cassettes 144, 164 for a rotary peristaltic pump and a linear or curvilinear peristaltic pump. In each configuration, a free end 114d of the tubing segment 114a may be attached to a connector 140, 160 which is braced or held in a desired position. The tubing segment 114a may be stretched by a force applicator 122 to stretch the tubing segment to a predetermined length. The amount of force necessary to stretch the tubing segment 114a is measured by the gauge or strain meter 134.

Cutting mechanism 130 is then adjusted to cut the tubing at a length correlated to the force required to stretch the tube to the desired length. Thus, for example, the tubing segment may reach the predetermined length with only 4 pounds of pulling force. The cutting mechanism 130 may be moved to position A and form the cut. In contrast, another tubing segment (either from another batch or even intrabatch) may require 5 pounds of pressure to draw the tubing to the desired length. This may correlate with the cutting mechanism 130 being moved to a position slightly further from the end of the tubing and then performing the cut. This results in tubing segments 114a which are of slightly different lengths. The differences in length help to minimize accuracy differences between tubing falling within the tolerances under which the tubing is obtained. The varied length tubing segments 114a reduce the accuracy variations in the pump cassettes 144, 164.

It will be appreciated that a method for forming a peristaltic pump cassette may include: applying a predetermined force to stretch a tubing segment; cutting the tubing segment at a predetermined length; and attaching the tubing segment to at least one connector to form a peristaltic pump cassette. The method may also include: subjecting the tubing segment to a force between 4 and 6 pounds; cutting the tubing segment so that the tubing segment under ambient conditions is between 4.9 inches and 5.1 inches; the tubing having an outer diameter of about 0.200 inches±0.003 inches and an inner diameter of about 0.120 inches±0.003 inches; one end of the tubing segment being attached to a connector prior to stretching; the tubing segment being drawn from bulk feedstock; the tubing segment being braced or anchored at one end prior to stretching; the bulk feed stock is a roll of tubing falling within a predetermined range of variations; and/or the tubing segment being attached to a connector prior to applying the predetermined force, or any combination thereof.

Likewise, a method for forming a peristaltic pump cassette may include; applying a force to a tubing segment to stretch the tubing segment to a predetermined length; cutting the tubing segment at a position correlated with the force necessary to stretch the tubing segment to the predetermined length; and attaching the tubing segment to at least one connector to form a peristaltic pump cassette. The method may also include: subjecting the tubing segment to a force between 4 and 6 pounds; cutting the tubing segment so that the tubing segment under ambient conditions is between 4.9 inches and 5.1 inches; the tubing having an outer diameter of about 0.200 inches±0.003 inches and an inner diameter of about 0.120 inches±0.003 inches; one end of the tubing segment being attached to a connector prior to stretching; the tubing segment being drawn from bulk feedstock; the tubing segment is braced or anchored at one end prior to stretching; the tubing segment being braced or anchored by attaching the tubing segment to a connector of the peristaltic pump cassette prior to stretching; and/or the bulk feedstock being a roll of tubing falling within a pre-determined range of variations, or combinations thereof.

Similarly, a method of improving accuracy in a pump cassette may include: selecting bulk tubing; stretching a segment of the tubing; cutting the segment of the tubing; and attaching at least one end of the segment of the tubing to a connector to form a pump cassette. The method may also include: the segment of the tubing being attached to a connector of a pump cassette prior to stretching of the segment of tubing; the segment of the tubing being stretched under a predetermined force; and/or the segment of the tubing being stretched to a predetermined length, or combinations thereof.

There is thus disclosed an improved method for forming enteral feeding and infusion pump cassettes. It will be appreciated that numerous changes may be made to the present invention without departing from the scope of the claims.

What is claimed is:

1. A method for forming a peristaltic pump cassette, the method comprising:
   attaching at least one connector to a tubing segment;
   applying a predetermined force to stretch the attached tubing segment;
   cutting the attached tubing segment at a predetermined length; and
   attaching the at least one connector with the tubing segment to the peristaltic pump cassette.

2. The method according to claim 1, wherein the method comprises subjecting the tubing segment to a force between 4 and 6 pounds.

3. The method according to claim 1, wherein the method comprises cutting the tubing segment so that the tubing segment under ambient conditions is between 4.9 inches and 5.1 inches.

4. The method according to claim 1, wherein the tubing has an outer diameter of about 0.200 inches±0.003 inches and an inner diameter of about 0.120 inches±0.003 inches.

5. The method according to claim 1, wherein the tubing segment is attached to the at least one connector at one end of the tubing.

6. The method according to claim 1, wherein the tubing segment is drawn from bulk feedstock and wherein the tubing segment is braced or anchored at one end prior to stretching.

7. The method according to claim 6, wherein the bulk feedstock is a roll of tubing falling within a predetermined range of variations.

8. The method according to claim 1, wherein the predetermined length is based at least in part on a physical characteristic of the tubing segment.

9. A method for forming a peristaltic pump cassette, the method comprising:
- attaching a connector to a tubing segment;
- applying a force to the attached tubing segment to stretch the tubing segment to a predetermined length;
- cutting the attached tubing segment at a position correlated with the force necessary to stretch the tubing segment to the predetermined length; and
- attaching the connector with the tubing segment to the peristaltic pump cassette.

10. The method according to claim 9, wherein the method comprises subjecting the tubing segment to a force between 4 and 6 pounds.

11. The method according to claim 9, wherein the method comprises cutting the tubing segment so that the tubing segment under ambient conditions is between 4.9 inches and 5.1 inches.

12. The method according to claim 9, wherein the tubing has an outer diameter of about 0.200 inches±0.003 inches and an inner diameter of about 0.120 inches±0.003 inches.

13. The method according to claim 9, wherein the tubing segment is attached to a connector at one end of the tubing prior to stretching.

14. The method according to claim 9, wherein the tubing segment is drawn from bulk feedstock and wherein the tubing segment is braced or anchored at one end prior to stretching.

15. The method according to claim 14, wherein the tubing segment is attached to the connector by a brace or anchor.

16. The method according to claim 14, wherein the bulk feedstock is a roll of tubing falling within a predetermined range of variations.

17. A method of improving accuracy in a pump cassette, the method comprising:
- selecting bulk tubing;
- attaching a first connector to a first end of the tubing;
- stretching a segment of the attached tubing;
- cutting the segment of the attached tubing; and
- forming the pump cassette by attaching a second end of the tubing to a second connector.

18. The method according to claim 17, wherein the segment of the tubing is stretched under a predetermined force.

19. The method according to claim 17, wherein the segment of the tubing is stretched to a predetermined length.

20. The method according to claim 17, wherein the predetermined length is based at least in part on a physical characteristic of the tubing segment.

* * * * *